United States Patent [19]

Thuillier, nee Nachmias et al.

[11] 4,197,309

[45] * Apr. 8, 1980

[54] 4-KETO-PHENOXYACETIC ACIDS

[75] Inventors: Germaine Thuillier, nee Nachmias; Jean E. Thuillier, both of Paris; Jacqueline S. Laforest, nee Boutillier du Retail, Vincennes; Bernard J. M. Cariou, Combleux; Pierre A. R. Bessin, Chilly-Mazarin; Jacqueline S. Bonnet, nee Roux, Paris, all of France

[73] Assignee: Albert Roland S.A., Paris, France

[*] Notice: The portion of the term of this patent subsequent to Apr. 12, 1994, has been disclaimed.

[21] Appl. No.: 911,040

[22] Filed: May 30, 1978

Related U.S. Application Data

[63] Continuation of Ser. No. 763,722, Jan. 13, 1977, abandoned.

[30] Foreign Application Priority Data

Oct. 12, 1976 [FR] France .................. 76 30584

[51] Int. Cl.² .................. A61K 31/38; A61K 31/34; C07D 333/24; C07D 307/12
[52] U.S. Cl. .................. 424/275; 424/285; 260/347.3; 549/72; 549/79
[58] Field of Search .................. 260/332.2 A, 347.3; 424/275, 285

[56] References Cited

U.S. PATENT DOCUMENTS

| 3,758,506 | 9/1973 | Godfroid et al. ............. 260/332.2 A |
| 3,989,838 | 11/1976 | Maass ..................................... 424/275 |
| 4,017,632 | 4/1977 | Thuillier et al. .............. 260/332.2 A |

Primary Examiner—Alan Siegel
Attorney, Agent, or Firm—Stevens, Davis, Miller & Mosher

[57] ABSTRACT

The invention provides certain 4-keto-phenoxyacetic acids and their oximes of the formula:

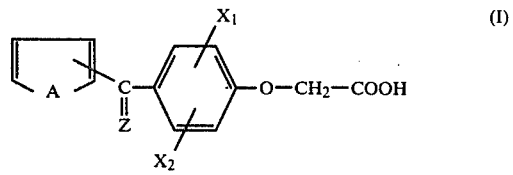

in which
A is selected from oxygen and sulphur,
Z is selected from oxygen and the group NOH, and
$X_1$ and $X_2$ are radicals independently selected from hydrogen, halogen and methyl, with the proviso that the benzene nucleus is never substituted by two halogen atoms in ortho-position with respect of one another, and pharmaceutically acceptable alkaline and amine addition salts thereof.

26 Claims, No Drawings

4-KETO-PHENOXYACETIC ACIDS

This is a continuation of application Ser. No. 763,722 filed Jan. 13, 1977, now abandoned.

SUMMARY OF THE INVENTION

The present invention relates to certain 4-keto-phenoxyacetic acids and their oximes as well as the pharmaceutically acceptable alkali or amine addition salts of these acids, their preparation and their therapeutic use as uricosuric non-diuretic agents.

DESCRIPTION OF THE INVENTION

The compounds according to the invention are those of the following general formula

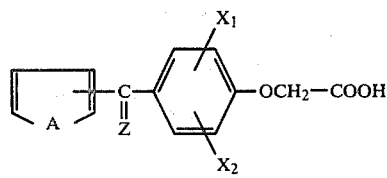  (I)

in which

A is selected from oxygen and sulphur,

Z is selected from oxygen and the group NOH, and $X_1$ and $X_2$ are radicals independently selected from hydrogen, halogen and methyl, with the proviso that the benzene nucleus is never substituted by two halogen atoms in ortho-position with respect to one another, and pharmaceutically acceptable alkaline and amine addition salts thereof.

Certain dihalogenated compounds of this type have been described in U.S. Pat. No. 3,758,506; these are uricosuric agents but above all powerful diuretic agents. However, in the treatment of certain conditions, for example gout, it is necessary to administer medicaments which are exclusively uricosuric, any associated diuretic effect being unwanted and, indeed, damaging. In addition, it is known that numerous diuretics currently used have a hyperuricemic effect, which necessitates the simultaneous administration of uricosurics in the treatment of certain cardiovascular illnesses and the compounds of formula I have a certain importance in this therapeutic area.

The compounds of formula I can be prepared by reacting, in an alkaline medium, a phenol of the formula II

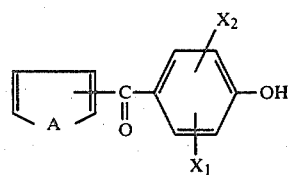  (II)

in which A, $X_1$ and $X_2$ have the meanings given above, with a compound of the formula $XCH_2COOR$ (III), in which X represents a halogen atom and R represents a hydrogen atom or an alkyl group. The compound so obtained is saponified when it is an ester (R=alkyl), and in appropriate cases the ketone can be reacted with hydroxylamine to obtain the oxime.

The ketones of the formula I (Z=O) can also be prepared by a Friedel Crafts type reaction between a heterocyclic acid chloride of the formula

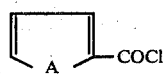  (IV)

and a phenol ether of the formula

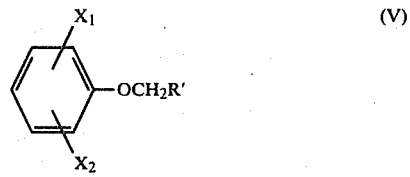  (V)

in which $X_1$, $X_2$ and A have the meanings given above and R' represents a hydrogen atom, a COOH or COOR" group, R" being an alkyl group.

When the reaction is carried out with a methylether (V, R=H), the compound of formula I is obtained by using a process known per se, which is demethylation by aluminium chloride or pyridine hydrochloride, followed by reaction on the phenol in a basic medium of chloro (or bromo) acetic acid or of one of its esters followed, if necessary, by a hydrolysis reaction.

When the compounds of the formula I carry on the benzene nucleus in the ortho-position to the other function at least one halogen substituent it is preferable to carry out the Friedel Crafts reactions on anisole, to demethylate the ether so obtained, and then to halogenate the benzene nucleus of the 4-keto phenol by the action of $Cl_2$, $Br_2$ or $I_2$ before preparing the phenoxy acetic acid ether.

The oximes of the formula I (Z=NOH) are prepared according to the invention by reacting a corresponding ketone with hydroxylamine. Conveniently this may be effected by the action of hydroxylamine hydrochloride on the ketone in solution in pyridine. The oximes are generally obtained in the form of a mixture of their two stereoisomers. The relative proportions of these two isomers of the carbimino group can be determined, for example, by nuclear magnetic resonance spectroscopy.

The acid salts of the compounds of formula I may be prepared by the action on the acid in solution in, for example, an alcohol or a ketone, of an alkaline hydroxide or a pharmaceutically acceptable amine.

The following Examples illustrate the invention but do not limit it. The compounds mentioned have been subjected to analytical study (elementary analysis, potentiographic titration, I.R. and N.M.R. spectra) and they are characterised by their melting points determined upon a Köfler bench.

EXAMPLE 1

4-(2-Thenoyl)-2,6-dimethyl-phenoxyacetic acid (A) (2-Thienyl) (3,5-dimethyl-4-methoxyphenyl)ketone Into a solution of 60 g of 2,6-dimethyl anisole and 62.7 g of the chloride of 2-thiophene carboxylic acid in 250 ml of anhydrous methylene chloride there was introduced over 30 minutes 58.5 g of aluminium chloride while maintaining the temperature at about 10° C. The reaction medium was brought to the reflux temperature of the solvent for 2½ hours, then poured onto one kg of crushed ice mixed with 150 ml of concentrated hydrochloric acid. The organic phase was decanted, the aqueous phase extracted with methylene chloride, and the organic phase washed with an aqueous solution of sodium hydroxide, then with water. After drying and evaporation of the solvent, 110 g of an oil was isolated which was distilled under reduced pressure to give 89 g of ketone. Boiling point (14 mm Hg)=225° C.

(B) (2-Thienyl) (3,5-dimethyl-4-hydroxyphenyl)ketone

A mixture of 20 g of the ketone obtained according to (A) and 46 g of pyridine hydrochloride were kept for 6 hours at 180° C. and then poured onto iced water. The mixture was extracted with ethyl ether, then with an aqueous solution of sodium hydroxide. After acidifying the solution, the phenol was extracted in ethyl ether, the solvent evaporated and the residual oil distilled to give 17 g of pure phenol. Boiling point (0.15 mm Hg)=185° C.—m.pt.=50° C.

(C) Ethyl-4-(2-Thenoyl)-2,6-dimethyl-phenoxyacetate

There was kept for 3 hours at 60° C. a solution in 150 ml of dimethylformamide of 10 g of the phenol obtained according to (B), 3 g of potassium hydroxide and 9 g of ethyl bromoacetate. The mixture was filtered, the solvent evaporated, the residue dissolved in ethyl ether, and the impurities extracted in a basic aqueous solution. After concentration of the solvent, 11.2 g of the ester were obtained which melted at 89° C.

(D) 4-(2-Thenoyl)-2,6-dimethyl-phenoxyacetic acid 11 g of the ester obtained according to (C) were dissolved in 150 ml of aqueous ethanol (50/50) containing 2.7 g of sodium hydroxide; the solution was kept for 3 hours at 95° C., the ethanol evaporated under reduced pressure and the aqueous phase acidified. 9.4 g of the acid precipitated - m.pt.=115° C.

EXAMPLE 2

4-(2-Thenoyl)-2,3-dimethyl-phenoxyacetic acid (A) (2-thienyl) (2,3-dimethyl-4-methoxyphenyl)ketone This compound was prepared in 86% yield by using step (A) of Example 1 with the chloride of 2-thiophene carboxylic acid and 2,3-dimethyl anisole.

(B) (2-Thienyl) (2,3-dimethyl-4-hydroxyphenyl)ketone 123 g of the preceding ether were dissolved in 1300 ml of benzene and there was introduced into the solution over a period of 1 hour 30 minutes 133 g of aluminium chloride. The mixture was kept for 5 hours at its reflux temperature and then poured onto a mixture of ice and hydrochloric acid. The phenol was extracted in ether and purified by dissolving in an aqueous solution of sodium hydroxide from which it precipitated by acidification. There was obtained 67 g of the product melting at 144° C.

(C) Ethyl-4-(2-Thenoyl)62,3-dimethyl phenoxyacetate

Into a solution of sodium ethylate prepared by the action of 2.3 g of sodium on 200 ml of ethanol, there was introduced 23.2 g of the phenol of step (B), 14.9 g of sodium iodide and 13.5 g of ethylchloroacetate. The mixture was kept under reflux for 8 hours, the hot solution filtered and the solvent evaporated, the phenol which had not reduced being eliminated from the residue by extraction in an aqueous sodium hydroxide solution. There was thus isolated after drying 22.15 g of pure acetate in the form of an oil.

(D) 4-(2-Thenoyl)-2,3-dimethyl-phenoxyacetic acid

This compound was obtained by hydrolysis of its ethyl ester in aqueous ethanol in the presence of potassium hydroxide. After recrystallisation in benzene or 1,2-dichloroethane the pure acid melted at 134° C.

EXAMPLE 3

4-(2-furoyl)-2,6-dibromo-phenoxyacetic acid (A) (2-Furyl) (3,5-dibromo-4-hydroxyphenyl)ketone There was introduced into a solution of 28 g sodium acetate and 60 ml methanol 19 g of (2-furyl) (4-hydroxyphenyl) ketone (m.pt.=164° C.) prepared according to the method described in Example 1 (A) and (B), and then there was introduced dropwise 11 ml of bromine dissolved in 14 ml of acetic acid. After 2 hours stirring at ambient temperature, the mixture was poured into three volumes of water and the precipitate isolated. After recrystallisation in dichloroethane there was obtained 22 g of phenol dibromide melting at 164° C.

(B) Ethyl-4-(2-furoyl)-2,6-dibromo-phenoxyacetate

There was kept under reflux for 6 hours 300 ml of methylethylketone containing 21 g of the phenol of step (A), 15 g of potassium carbonate and 18 g of ethylbromoacetate. After hot filtration the solvent was evaporated and the solid recrystallised in ethanol. 21 g of the ester were obtained, which melted at 114° C.

(C) 4-(2-furoyl)-2,6-dibromo-phenoxyacetic acid

This compound was obtained by hydrolysis of its ester from step (B) in aqueous ethanol (50/50) in the presence of potassium carbonate with 90% yield. It melted at 167° C.

EXAMPLE 4

4-[(2-thienyl)hydroxyiminomethyl]-2,6-dimethyl-phenoxyacetic acid 4 g of 4-(2-thenoyl)-2,6-dimethyl-phenoxyacetic acid and 4 g of hydroxylamine hydrochloride were dissolved in 30 ml of pyridine and the mixture was kept for 3 hours at reflux. The mixture was then poured into an N aqueous solution of hydrochloric acid and the oxime extracted in ethyl ether. The remaining solid, after evaporation of the solvent, was a mixture of the two isomers of the oxime which melted at 152° C.

EXAMPLE 5

4-(2-thenoyl)-2,6-diiodo-phenoxyacetic acid (A) (3,5-Diiodo-4-hydroxyphenyl) (2-thienyl) ketone and (3-iodo-4-hydroxyphenyl) (2-thienyl) ketone Into a solution of 50 g of (4-hydroxyphenyl) (2-thienyl) ketone, in 400 ml of a 3% aqueous solution of sodium hydroxide there was introduced slowly 76.2% of iodine and 104 g of potassium iodide in solution in 400 ml water. After 12 hours stirring the precipitate was removed, and then a 5% aqueous solution of sodium bisulphite introduced until the pH was acid. The precipitate which appeared was isolated. It contained the mono and diiodo phenols which could be separated due to their differences in solubility in chloroform. There was thus obtained after recrystallisation in ethanol 14 g of the (3,5-diiodo-4-hydroxyphenyl) (2-thienyl) ketone which melted at 158° C. and 40.2 g of (3-iodo-4-hydroxyphenyl) (2-thienyl) ketone: m.pt. = 190° C. (recrystallisation in aqueous dioxane (50/50)).

(B) Ethyl-4-(2-Thenoyl)-2,6-diiodo-phenoxyacetate

The sodium salt was prepared from 13.65 g of phenol by the action of 2 g of sodium methylate in methanol. The mixture in solution was poured into 100 ml of dimethylformamide, the methanol removed and 6.2 g of ethylbromoacetate were introduced. After 12 hours at ambient temperature there was introduced into the medium 3 volumes of water and the mixture extracted with ethyl ether. The ethereal phase was washed with aqueous sodium hydroxide solution, then with water, dried, and the solvent removed. The ester was recrystallised in 95% aqueous ethanol.

There was obtained 9 g of ester which melted at 93° C.

(C) 4-(2-Thenoyl)-2,6-diiodo-phenoxyacetic acid

This was prepared starting from its ester with 90% yield by hydrolysis in aqueous ethanol in the presense of $K_2CO_3$. It melted at 160° C.

EXAMPLE 6

4-(2-Thenoyl)-2-iodo-phenoxyacetic acid (A) Ethyl-4-(2-Thenoyl)-2-iodo-phenoxyacetate This compound was prepared by using the method described in Example 5 (B). It melted at 123° C. after recrystallisation in ethanol.

(B) 4-(2-thenoyl)-2-iodo-phenoxyacetic acid

This was prepared by hydrolysis of its ethyl ester with 97% yield. It melted at 164° C.

EXAMPLE 7

4-(2-Thenoyl)-2-bromo-phenoxyacetic acid (A) Ethyl-4-(2-Thenoyl)-2-bromo-phenoxyacetate This ester was prepared with 95% yield by reaction of ethylbromoacetate with (3-bromo-4-hydroxyphenyl) (2-thienyl) ketone. The product was an oil.

(B) 4-(2-Thenoyl)-2-bromo-phenoxyacetic acid

This acid was obtained by hydrolysis in a basic medium of its ethyl ester. It melted at 180° C.

The following Table I lists the structural formula and melting points of each of the compounds of the above Examples 1 to 7, together with structural formula and melting points for additional Examples 8 to 16 of compounds prepared in like manner.

TABLE I

| Example | Structural formula | M.Pt. (°C.) |
| --- | --- | --- |
| 1 | [thienyl-C(=O)-phenyl(2,6-diCH₃)-O-CH₂-COOH] | 115 |
| 2 | [thienyl-C(=O)-phenyl(2,3-diCH₃)-O-CH₂-COOH] | 134 |
| 3 | [furyl-C(=O)-phenyl(2,6-diBr)-O-CH₂-COOH] | 167 |
| 4 | [thienyl-C(=NOH)-phenyl(2,6-diCH₃)-O-CH₂-COOH] | 152 |
| 5 | [thienyl-C(=O)-phenyl(2,6-diI)-O-CH₂-COOH] | 160 |
| 6 | [thienyl-C(=O)-phenyl(2-I)-O-CH₂-COOH] | 164 |
| 7 | [thienyl-C(=O)-phenyl(2-Br)-O-CH₂-COOH] | 180 |
| 8 | [thienyl-C(=O)-phenyl(2-Cl)-O-CH₂-COOH] | 120 |
| 9 | [thienyl-C(=O)-phenyl(2,6-diBr)-O-CH₂-COOH] | 140 |
| 10 | [thienyl-C(=NOH)-phenyl(2-Cl)-O-CH₂-COOH] | 144 |
| 11 | [thienyl-C(=NOH)-phenyl(2,6-diBr)-O-CH₂-COOH] | 180 |
| 12 | [furyl-C(=NOH)-phenyl(2,6-diBr)-O-CH₂-COOH] | 190 |
| 13 | [thienyl-C(=NOH)-phenyl(2,6-diI)-O-CH₂-COOH] | 195 |
| 14 | [thienyl-C(=NOH)-phenyl-O-CH₂-COOH] | 164 |
| 15 | [furyl-C(=NOH)-phenyl-O-CH₂-COOH] | 193 |
| 16 | [thienyl-C(=NOH)-phenyl(2-Br)-O-CH₂-COOH] | 202 |

The compounds of the invention have been subjected to different pharmacological tests which have revealed in particular their value as uricosuric agents. The following results illustrate this property.

The uricosuric activity was studied on lots of 5 rats weighing 250 to 280 g. The compounds of the invention were administered to the animals orally in doses of from 5 to 200 mg/kg. One hour after this administration and anaesthesia with ether, the animals received an intravenous injection of 1 cm3 of an aqueous 1% solution of phenol red. Samples of blood were taken 15, 30, 45 and 60 minutes after this injection and the quantity of blood phenol red measured. This method is described by H. C. SCARBOROUGH and G. R. McKINNEY in J. Med. Pharm. Chem. 5 175 (1962) and E. KREPPEL in Med. Exptl. 1 285 (1959).

All the compounds of the invention diminish the speed of elimination of phenol red in the rat at the dosages mentioned and can thus be considered specifically uricosuric agents. In the following Table II there are set out the results obtained with the administration of a certain of the compounds as well as with the administration of benziodarone, a uricosuric agent currently used in human therapy. It can be stated that the uricosuric activity of all the compounds at 100 mg/kg is at least equivalent or higher than that of benziodarone.

Since in addition the $LD_{50}$ of all the compounds of the invention, determined by the method of C. I. BLISS Quart. J. Pharm. Pharmacol. 2 192–216 (1938) is orally greater than 1000 mg/kg, it can be seen that the therapeutic index of the compounds of formula I and of their salts permit their use in human therapy in daily doses of from 10 mg to 1 g.

The compounds of the invention can be administered orally or parenterally, optionally in association with known vehicles such as excipients or diluents, for example, in the form of gelatine capsules, tablets or solutions.

Thus, the invention includes a pharmaceutical composition, which composition comprises a compound of formula I or a pharmaceutically acceptable alkali or amine addition salt thereof, together with a pharmaceutically acceptable vehicle.

The invention also includes a method of inducing a uricosuric effect in a patient without significant diuresis, which method comprises administering a compound of formula I, a pharmaceutically acceptable alkali or amine addition salt thereof, or a composition as defined above.

TABLE II

| Example No | Dose mg/kg | Uricosuric activity (% of retention of phenol red with reference to the control animals) | | | |
|---|---|---|---|---|---|
| | | after 15 minutes | after 30 minutes | after 45 minutes | after 60 minutes |
| 2 | 50 | +61 | +88 | +86 | +160 |
| 5 | 50 | +113 | +100 | +93 | +79 |
| | 25 | +78 | +66 | +50 | +71 |
| 6 | 50 | +59 | +88 | +84 | +35 |
| | 25 | +88 | +111 | +92 | +52 |
| 9 | 100 | +69 | +75 | +100 | +75 |
| | 50 | +52 | +59 | +80 | +65 |
| 11 | 50 | +55 | +43 | +65 | +40 |
| benziodarone | 100 | +37 | +50 | +53 | +18 |

We claim:
1. A compound of the formula

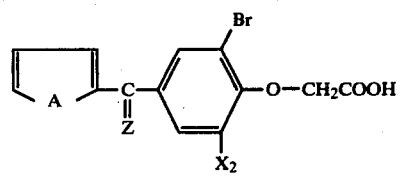

wherein
$X_2$ is hydrogen or bromo
A is oxygen or sulfur
Z is oxygen or NOH
or a pharmaceutically acceptable alkaline or amine addition salt thereof.

2. A compound of claim 1 wherein $X_2$ is bromo.
3. A compound of claim 1 wherein Z is oxygen.
4. A compound of claim 1, wherein Z is sulfur.
5. A compound of claim 3 which is 4-(2-thenoyl)-2,6-dibromo-phenoxyacetic acid or its oxime or pharmaceutically acceptable alkaline or amine addition salt thereof.
6. A method of inducing a uricosic effect in a patient without significant diuresis, which comprises administering to said patient an effective amount of a compound of claim 1 to induce said uricosic effect.
7. A compound of the formula

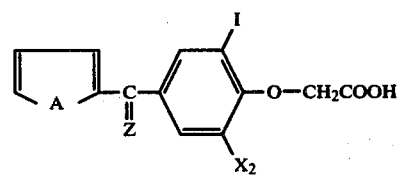

wherein
$X_2$ is iodo or hydrogen
A is oxygen or sulfur
Z is oxygen or NOH
or a pharmaceutically acceptable alkaline or amine addition salt thereof.

8. A compound of claim 7 wherein $X_2$ is iodo.
9. A compound of claim 7 wherein A is oxygen.
10. A compound of claim 7 wherein A is sulfur.
11. A compound of claim 7 wherein Z is NOH.
12. A compound of claim 10 wherein said compound is 4-(2-thenoyl)-2-iodo-phenoxy-acetic acid, its oxime or a pharmaceutically acceptable alkaline or amine addition salt thereof.
13. A compound of claim 10 wherein said compound is 4-(2-thenoyl)-2,6-diido-phenoxyacetic acid, its oxime or a pharmaceutically acceptable alkaline or amine addition salt thereof.
14. A method of inducing a uricosic effect in a patient without significant diuresis, which comprises administering to said patient an effective amount of a compound of claim 7 to induce said uricosic effect.
15. A compound of the formula

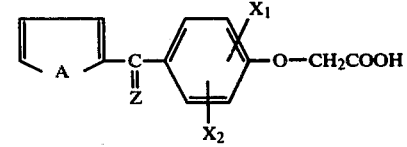

wherein

A is oxygen or sulfur

Z is oxygen or NOH each of X and $X_2$ is independently hydrogen or methyl or a pharmaceutically acceptable alkaline or amine addition salt thereof.

16. A method of inducing a uricosic effect in a patient without significant diuresis, which comprises administering to said patient an effective amount of a compound of claim 15 to induce said uricosic effect.

17. A compound of the formula

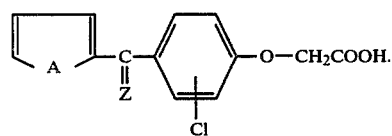

wherein

A is oxygen or sulfur

Z is oxygen or NOH or a pharmaceutically acceptable alkaline or amine addition salt thereof.

18. A method of inducing a uricosic effect in a patient without significant diuresis, which comprises administering to said patient an effective amount of a compound of claim 17 to induce said uricosic effect.

19. A compound of the formula

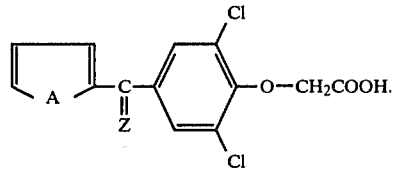

wherein

A is oxygen or sulfur

Z is oxygen or NOH or a pharmaceutically acceptable alkaline or amine addition salt thereof.

20. A method of inducing a uricosic effect in a patient without significant diuresis, which comprises administering to said patient an effective amount of a compound of claim 19 to induce said uricosic effect.

21. A pharmaceutical composition capable of inducing a uricosic effect to a patient without significant diuresis, which comprises an effective amount of a compound of claim 1 to provide said uricosic effect.

22. A pharmaceutical composition capable of inducing a uricosic effect to a patient without significant diuresis, which comprises an effective amount of a compound of claim 7 to provide said uricosic effect.

23. A pharmaceutical composition capable of inducing a uricosic effect to a patient without significant diuresis, which comprises an effective amount of a compound of claim 12 to provide said uricosic effect.

24. A pharmaceutical composition capable of inducing a uricosic effect to a patient without significant diuresis, which comprises an effective amount of a compound of claim 15 to provide said uricosic effect.

25. A pharmaceutical composition capable of inducing a uricosic effect to a patient without significant diuresis, which comprises an effective amount of a compound of claim 17 to provide said uricosic effect.

26. A pharmaceutical composition capable of inducing a uricosic effect to a patient without significant diuresis, which comprises an effective amount of a compound of claim 19 to provide said uricosic effect.

* * * * *